(12) United States Patent
Baidaoui et al.

(10) Patent No.: US 12,372,403 B2
(45) Date of Patent: Jul. 29, 2025

(54) COLOR MEASURING DEVICE FOR A FLUID DISTRIBUTION SYSTEM

(71) Applicant: EXEL INDUSTRIES, Epernay (FR)

(72) Inventors: Ahmed Baidaoui, Sainte Genevieve des Bois (FR); Boussif Khaldi, Arnouville (FR); Philippe De Talhouet, Paris (FR); Nicolas Ferrere, Precy sur Oise (FR)

(73) Assignee: EXEL INDUSTRIES, Epernay (FR)

( * ) Notice: Subject to any disclaimer, the term of this patent is extended or adjusted under 35 U.S.C. 154(b) by 327 days.

(21) Appl. No.: 17/947,153

(22) Filed: Sep. 18, 2022

(65) Prior Publication Data

US 2023/0086515 A1 Mar. 23, 2023

(30) Foreign Application Priority Data

Sep. 23, 2021 (FR) ...................................... 2110045

(51) Int. Cl.
*G01J 3/02* (2006.01)
*G01J 3/26* (2006.01)

(52) U.S. Cl.
CPC .............. *G01J 3/26* (2013.01); *G01J 3/0294* (2013.01)

(58) Field of Classification Search
CPC .. G01J 3/26; G01J 3/0294; G01J 3/46; G01N 1/2035
See application file for complete search history.

(56) References Cited

U.S. PATENT DOCUMENTS

| 6,888,636 B2 * | 5/2005 | Martino | G01N 21/05 356/319 |
| 10,031,025 B2 * | 7/2018 | Berghaus | G01J 3/463 |
| 10,340,651 B1 * | 7/2019 | Drummer | H01S 3/094003 |
| 2004/0056264 A1 * | 3/2004 | Hisano | G01N 21/474 438/22 |
| 2008/0118204 A1 * | 5/2008 | Ankerhold | G02B 6/3604 385/51 |

(Continued)

FOREIGN PATENT DOCUMENTS

| DE | 3922902 A1 | 1/1991 |
| EP | 2783200 A2 | 1/2014 |

(Continued)

OTHER PUBLICATIONS

INPI Search Report for FR 2110045, May 16, 2022, 2 pages.
English translation for publication No. DE3922902A1, Jan. 17, 1991, 2 pages.

*Primary Examiner* — Abdullahi Nur
(74) *Attorney, Agent, or Firm* — Soquel Group LLC

(57) ABSTRACT

A tint measuring device configured for being connected in series in a fluid flow circuit, the tint measuring device including at least one light source configured for emitting polychromatic light towards the fluid in a measurement zone; a light sensor configured for receiving a light signal either reflected from or transmitted through the fluid, the reflected or the transmitted light signal corresponding to the optical reflection or the optical transmission, respectively, by the fluid, of the polychromatic light emitted towards the fluid by the at least one light source; and a computing unit configured for performing a spectral analysis of the light signal received by the light sensor and for determining a chromatic signature of the fluid.

13 Claims, 4 Drawing Sheets

(56) References Cited

U.S. PATENT DOCUMENTS

2008/0297809 A1* 12/2008 Holzapfel .............. G01D 5/266
356/614
2016/0047733 A1* 2/2016 Takeda ............... G01N 15/1459
435/7.1

FOREIGN PATENT DOCUMENTS

| WO | 02074866 A2 | 9/2002 |
| WO | 02074866 A3 | 9/2002 |
| WO | 2013076512 A2 | 5/2013 |
| WO | 2013076512 A3 | 5/2013 |

* cited by examiner

COLOR MEASURING DEVICE FOR A FLUID DISTRIBUTION SYSTEM

CROSS-REFERENCE TO RELATED APPLICATION

This application is a U.S. non-provisional application claiming the benefit of French Application No. 21 10045, filed on Sep. 23, 2021, the contents of which are incorporated herein by reference in their entirety.

FIELD OF THE INVENTION

The present invention relates to the field of fluid dispensing, in particular spray painting. In particular, the present invention relates to a tint measuring device suitable for performing an identification of the tint of the fluid flowing through a fluid flow circuit intended for being dispensed, and in particular for supervising operations or phenomena involving a change of tint in such a fluid dispensing system.

BACKGROUND OF THE INVENTION

As is known, a fluid dispensing system generally includes at least one fluid reservoir, a dispensing end member, and a fluid flow circuit directing fluid from the at least one fluid reservoir to the dispensing end member, e.g., a spray gun.

In the context of a spray paint dispensing system, it is known how to produce, upstream of the spray gun, a mixture of two or three components, e.g., a paint and a catalyst, the optimum ratio of the composition being provided by the paint manufacturer. It is interesting to be able to monitor the composition ratio of the paint before same is sprayed, in order to be able to adjust the composition ratio if need be, e.g. using a valve control system.

Furthermore, during a tint change operation, e.g., a tint intensification, a change of color, or a rinsing of the paint dispensing system with a solvent, it is known how to carry out a visual inspection of the sprayed fluid in order to confirm that the transition operation has been completed. Alternatively, it is known how to confirm that the transition operation is completed on the basis of a predefined time delay. In fact, the duration of tint change operations is not optimized, which leads to waste and consequently affects the purchase costs of components and the recycling costs.

SUMMARY OF THE DESCRIPTION

In response to such drawbacks, the present invention proposes a tint measuring device configured for measuring the tint of a fluid, in particular during tint changing operations. Thus, the present invention advantageously makes it possible to limit the waste of fluid and of the constituents thereof.

More precisely, a subject matter of one aspect of the invention relates to a tint measuring device configured for being connected in series in a fluid flow circuit, the tint measuring device comprising at least one light source, a light sensor, and a computing unit. The at least one light source is configured for emitting polychromatic light towards the fluid in a measurement area. The light sensor is configured for receiving a light signal either reflected from or transmitted through the fluid, the reflected or transmitted light signal corresponding to the optical reflection or, to the optical transmission, respectively, by the fluid, of the polychromatic light emitted towards the fluid by the at least one light source. The computing unit is configured for performing a spectral analysis of the light signal received by the light sensor and for determining a chromatic signature of the fluid.

The computing unit is further configured for determining a brightness level of the light signal received by the light sensor.

The tint measuring device according to the invention can be used for performing a chromatic analysis of the fluid, and consequently offers the considerable advantage of making possible, a rapid and reliable identification of the tint of the fluid, and an improved control of the operations of changing the tint of the fluid, in particular, a tint intensification, a change of paint color, or a rinse in the context of a paint dispensing system. Thus, the present invention improves the efficiency of such operations of change of tint of the fluid, and consequently substantially limits the waste of fluid components, thereby reducing purchase costs as well as recycling costs. Moreover, the series connection of the tint measuring device to the fluid flow circuit advantageously provides a more reliable measurement of the tint in the fluid flow circuit.

Preferentially, the tint measuring device according to the invention includes at least one acquisition optical fiber configured for directing the light signal either reflected from or transmitted through the fluid to the light sensor, the light sensor being remote from the measurement zone. Such configuration has the considerable advantage of moving the electronic components of the light sensor away from the measurement area, which can be subject to ATEX ("explosive atmosphere") regulations. Thus, it is possible to use a standard light sensor, which is less expensive. Moreover, the light sensor is advantageously distant from possible mechanical vibrations of the fluid flow circuit, further simplifying the design of the light sensor.

Preferentially, the tint measuring device according to the invention includes a chamber, for example opaque, through which is formed a fluid flow path configured for being connected on either side to the fluid flow path, the chamber, for example opaque, housing one end of each of the at least one acquisition optical fiber. The opaque chamber advantageously makes it possible to greatly limit any light pollution coming from the external medium during the tint measurements.

Advantageously, the tint measuring device according to the invention includes an end body encapsulating the end or ends of the at least one acquisition optical fiber.

The tint measuring device further includes an observation window arranged tangentially to the fluid flow stream.

The tint measuring device further includes a retaining element mounted in the chamber, for example opaque, for holding the observation window in position and for providing the leak-tightness of the fluid flow stream.

The end body is configured for being inserted, here into the chamber, for example opaque, in a removable manner, preferably into a pressing box of the chamber, so as to position the end body opposite the observation window. The end body has the advantage of simplifying the operations of assembling or disassembling the end body. During, e.g., a maintenance operation of the tint measuring device, the end body may be replaced, as a background task, during the spraying of the fluid, in other words without disturbing the flow of the fluid through the stream.

Advantageously, the tint measuring device according to the invention includes at least one lighting optical fiber connected at one end to the at least one light source and configured for directing the polychromatic light from the at least one light source towards the fluid. Moreover, the end body preferentially encapsulates the end or ends of the at least one lighting optical fiber. Thus, the configuration of the end body encapsulating, in the same body, the at least one lighting optical fiber and at least one acquisition optical fiber, facilitates the design and use of the tint measuring device according to the invention.

Advantageously, the end body includes an anti-reflection element arranged so as to optically isolate the at least one lighting optical fiber and the at least one acquisition optical fiber from one another, so as to limit the direct transmission of light from the at least one lighting optical fiber to the at least one acquisition optical fiber. The anti-reflection element advantageously makes it possible to limit the light pollution of the at least one acquisition optical fiber by the at least one lighting optical fiber.

Advantageously, the end body having a central axis, the ends of the at least one lighting optical fiber and at least one acquisition optical fiber being distributed circularly around the central axis of the end body at two different radial distances from the central axis, respectively, of the end body. Moreover, the end body includes an annular recess on a face configured for facing the measurement zone, the annular recess being arranged in a portion about the central axis and having a radius included between the two different radial distances. The end body then includes the anti-reflection element housed in the annular recess so as to optically isolate the at least one lighting optical fiber and the at least one acquisition optical fiber from one another.

According to one aspect of the invention, the invention relates to a fluid dispensing system including the fluid flow circuit and the tint measuring device according to another aspect of the invention described above, the tint measuring device being connected in series in the fluid flow circuit.

Advantageously, the fluid dispensing system according to such aspect of the invention consists of a paint dispensing system.

According to one aspect of the invention, the invention relates to a method for measuring the tint of a fluid flowing in a fluid flow circuit using a tint measuring device including at least one light source, a light sensor, and a computing unit, the process including the following operations:
  the emission of polychromatic light towards the fluid via the at least one light source;
  the reception by the light sensor of the light signal either reflected from or transmitted through the fluid;
  performing a spectral analysis by the computing unit of the light signal received by the light sensor so as to determine a chromatic signature of the fluid; and
  the comparison of the chromatic signature of the fluid with a chart of target chromatic signatures by the computing unit so as to determine the tint of the fluid.

Advantageously, the spectral analysis of the light signal includes the decomposition of the light signal in the RGB color system, the chromatic signature of the fluid including an RGB color code.

Advantageously, the method of measuring the tint according to such aspect of the invention, implemented during an operation of changing the tint of the fluid in the fluid flow circuit, includes determining that the tint change operation is completed when the fluid chromatic signature reaches a target chromatic signature for a predefined time, the target chromatic signature consisting of a subset of the target chromatic signature chart.

According to one aspect of the invention, the method further includes determining a brightness level, or clear, from the light signal received by the light sensor, more specifically from by the computing unit.

The method of measuring the tint according to this aspect, carried out during operation of rinsing and/or of tint intensification in the fluid flow circuit, includes determining that the operation is completed when the fluid chromatic signature reaches a target chromatic signature for a predefined time and/or when the brightness level reaches a desired value.

According to one aspect of the invention, the invention relates to a paint dispensing method including the tint measurement method as described above, the operation of changing the tint of the fluid in the fluid flow circuit comprising an operation of tint intensification, of change of color, or of rinsing.

BRIEF DESCRIPTION OF THE DRAWINGS

The invention will be better understood upon reading the following description, given only as an example, and referring to the enclosed drawings given as examples, but not limited to, wherein identical references are given to similar objects and wherein.

It should be noted that the figures show the invention in detail so that the invention can be implemented, the figures being of course useful for better defining the invention if need be.

DETAILED DESCRIPTION

The invention relates to a tint measuring device for a fluid dispensing system, wherein the fluid may have a wide viscosity range from low viscosity to high viscosity. The invention is described hereinafter in the context of a paint dispensing system, in particular by spraying. However, the invention is not limited to such particular application and the invention may be implemented in any fluid dispensing system suitable for directing a fluid, wherein it is advantageous to identify the tint of the fluid, in particular for supervising operations or phenomena involving a change of tint of the fluid.

In general, the paint dispensing system includes at least one reservoir of paint components, a dispensing end member, also referred to as a dispensing head, and a fluid flow circuit having ducts and fluidically connecting, via pipes, the at least one fluid reservoir to the dispensing end member. The terminal dispenser member may, e.g., include a spray gun.

Figure 1:
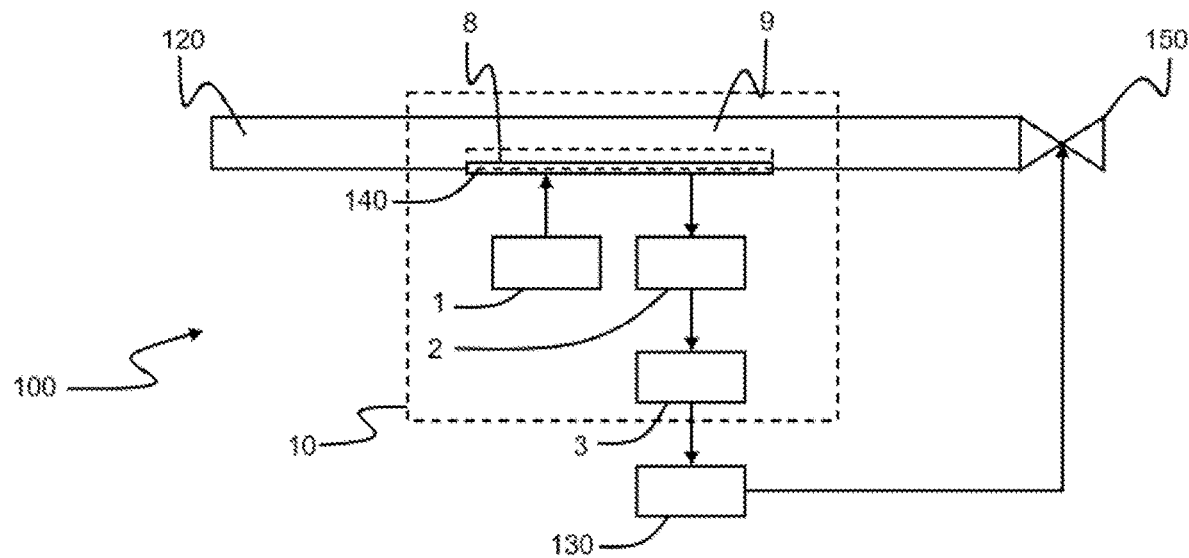
FIG. 1 is a schematic representation of a fluid dispensing system comprising a tint measuring device according to a first embodiment of the invention.

With reference to FIG. 1, according to one aspect of the invention, the invention relates to a tint measuring device 10 configured for being connected in series in a fluid flow circuit 120. Tint measuring device 10 according to such aspect of the invention includes at least one light source 1 configured for emitting polychromatic light toward the fluid in a measurement zone 140, a light sensor 2 configured for receiving a light signal either reflected from or transmitted through the fluid, and a computing unit 3 configured for performing spectral analysis of the light signal received by light sensor 2 so as to determine a chromatic signature of the fluid. The reflected or transmitted light signal corresponds to the optical reflection or to the optical transmission, respectively, by the fluid, of the polychromatic light emitted toward the fluid by the at least one light source 1. In a preferred embodiment, the polychromatic light is white light. In a variant, light source 1 may include a plurality of monochromatic sources of different corresponding wavelengths, e.g., a red laser source, a green laser source, and a blue laser source.

In one embodiment, computing unit 3 is further configured for determining a brightness level of the light signal received by light sensor 2.

The analysis, notably including the chromatic analysis, of the fluid as provided for by the invention has the considerable advantage of making possible a rapid and reliable identification of the tint of the fluid, and consequently an improved control of the operations of changing the tint of the fluid, in particular tint intensification, change of color of the paint, or rinsing of the paint dispensing system with a solvent, e.g. water. The present invention has the considerable advantage of improving the efficiency of such operations of change of tint of the fluid, and consequently substantially reducing waste of paint and solvent components, thereby reducing purchase costs as well as recycling costs.

In particular, the connection in series of tint measuring device 10 to fluid flow circuit 120 advantageously provides a more reliable measurement of tint in fluid flow circuit 120.

The polychromatic light preferably consists of white light, and the at least one light source 1 preferably consists of one or more light-emitting diodes, also referred to as LEDs. Moreover, the at least one light source 1 may be configured for emitting pulsed light.

Light sensor 2 preferably consists of a color sensor, in particular an RGB (Red Green Blue) color sensor.

Alternatively, light sensor 2 is able to sense the color, for example the RGB color, and also a brightness level.

Light sensor 2 may be positioned close to measurement zone 140. However, quality of the dispensed fluid or the environment thereof may often lead to constraints of compliance with ATEX ("explosive atmosphere") regulations, as in the context of the paint dispensing system. However, the use of a light sensor compatible with such constraint may be expensive and the integration thereof into tint measuring device 10 may be complex, or even impossible.

Figure 6:
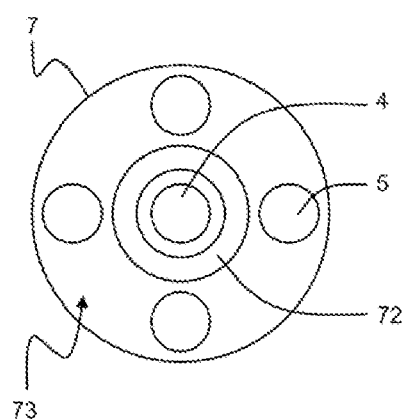
FIG. 6 is a schematic representation of a view of an end body of an example of a tint measuring device according to the invention.

To address such constraints, tint measuring device 10 according to the invention may preferentially include at least one acquisition optical fiber 4, e.g. a single acquisition optical fiber 4 as shown in FIG. 6, configured for directing the light signal either reflected from or transmitted through the fluid, to light sensor 2. In addition, light sensor 2 is then configured for being remote from measurement zone 140. Such configuration has the considerable advantage of moving the electronic components of light sensor 2 away from the ATEX zone, and thus of being apt to use a standard light sensor. Moreover, light sensor 2 is advantageously distant from possible mechanical vibrations of fluid flow circuit 120, which further simplifies the design of light sensor 2.

Furthermore, installation of the at least one acquisition optical fiber 4 and of light sensor 2 offset with respect to measurement zone 140 advantageously makes it possible to share a light sensor between a plurality of distinct measurement zones 140. However, where appropriate, a sequencing module has to be provided in the device according to the invention, configured so that the light emissions from the at least one light source 1 are synchronized, so as to prevent the light signals received by light sensor 2 from intersecting, and hence distorting the measurement.

Figure 5A:
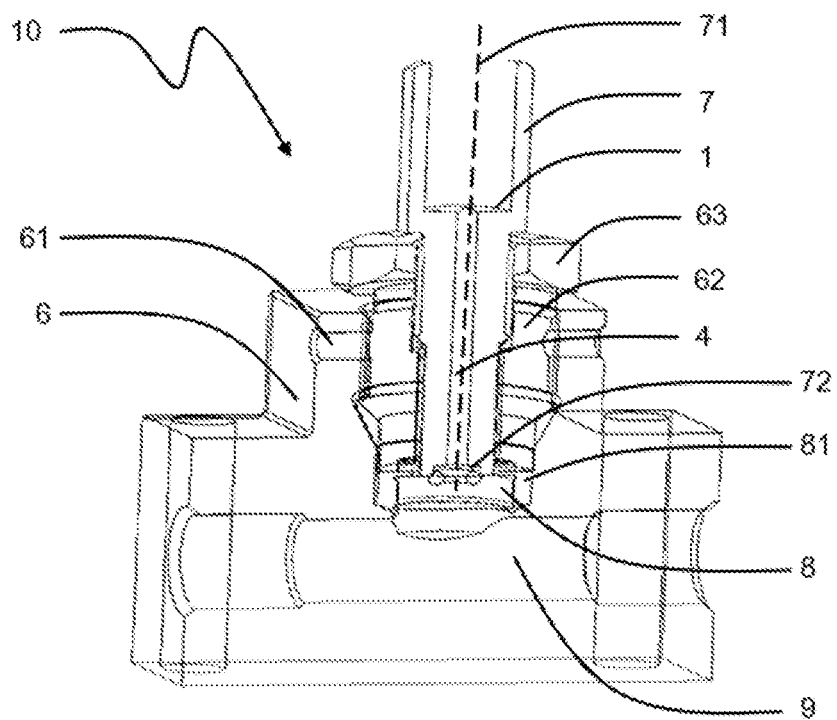
FIG. 5A is a schematic representation of a partial sectional view of an example of a tint measuring device according to the first embodiment of the invention.

Moreover, with reference to FIG. 5A, tint measuring device 10 preferably includes a chamber 6, for example opaque, through which a fluid flow stream 9 is formed, arranged for being connected on either side to fluid flow circuit 120. In particular, chamber 6, for example opaque, houses one end of each of the at least one acquisition optical fiber 4. Chamber 6, for example opaque, advantageously makes it possible to greatly limit any light pollution coming from the external environment during tint measurements. Moreover, chamber 6, for example opaque, includes in particular, means for holding the corresponding end or ends, e.g. a sheath.

With reference to FIG. 6, tint measuring device 10 may further include at least one lighting optical fiber 5 connected at one end to the at least one light source 1 and configured for directing polychromatic light from the at least one light source 1 toward the fluid. In particular, the number of optical lighting fibers 5 and the number of light sources 1 are suitable for providing a sufficient light intensity so that the reflected or the transmitted light signal has in turn a sufficient light intensity for carrying out the tint measurement. The number of lighting optical fibers 5 may correspond in particular to the number of light sources 1, e.g. four.

FIGS. 1-4 show different possible arrangements of the at least one light source 1 and light sensor 2.

In particular, according to a first embodiment of the invention shown in FIG. 1, analysis of the fluid is carried out on the basis of a light signal reflected from the fluid. In such first embodiment of the invention, the emission of light by the at least one light source 1 and the reception of the light signal reflected from the fluid are carried out on the same side of fluid flow stream 9. Such a configuration leads to measuring the tint substantially on the surface of the fluid. The first embodiment of the invention has the advantage of providing high compactness for tint measuring device 10, and of facilitating integration of tint measuring device 10 into the paint dispensing system, in particular via the extent of measurement zone 140 which is reduced to a limited portion of fluid flow stream 9.

Figure 2:
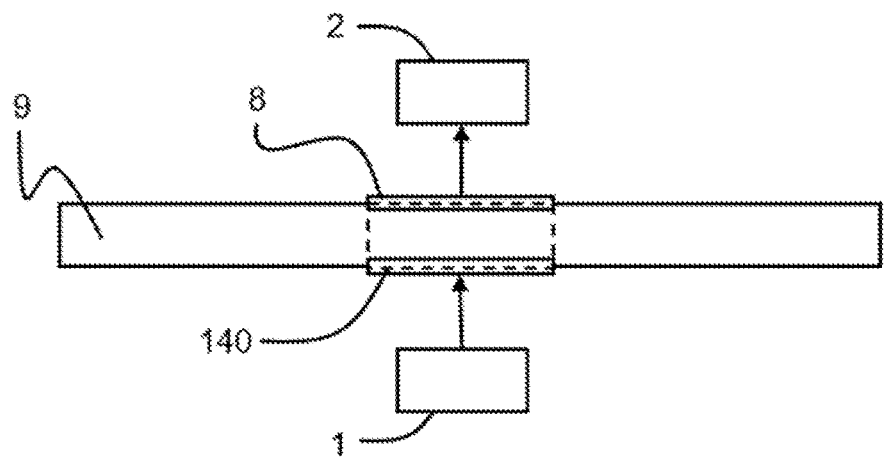
FIG. 2 is a schematic representation of a tint measuring device according to a second embodiment of the invention.

According to a second embodiment of the invention, represented in FIG. 2, analysis of the fluid is carried out on the basis of the light signal transmitted through the fluid. In this second embodiment of the invention, emission of light by the at least one light source 1 and reception of the light signal transmitted through the fluid are carried out respectively on either side of fluid flow stream 9. Such configuration makes it possible to perform a tint measurement through a section of the fluid, and hence improves the accuracy of tint measurement to the detriment however of the compactness of tint measurement device 10 and of the integration of tint measuring device 10 into the paint dispensing system.

Figure 3:
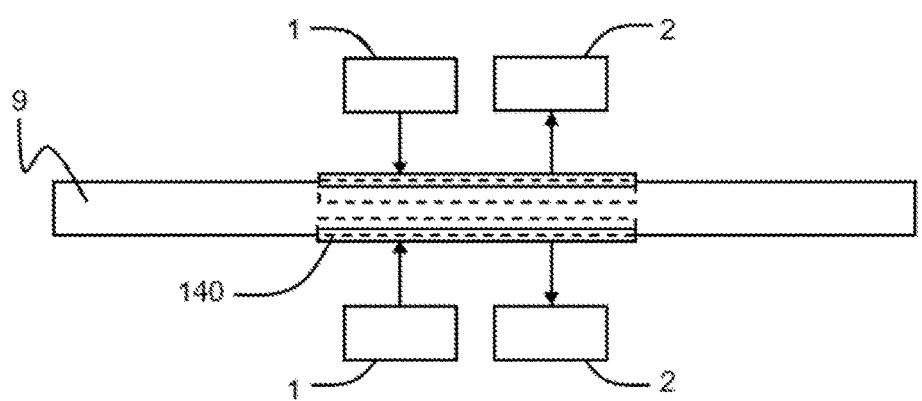
FIG. 3 is a schematic representation of a tint measuring device according to a third embodiment of the invention.
Figure 4:
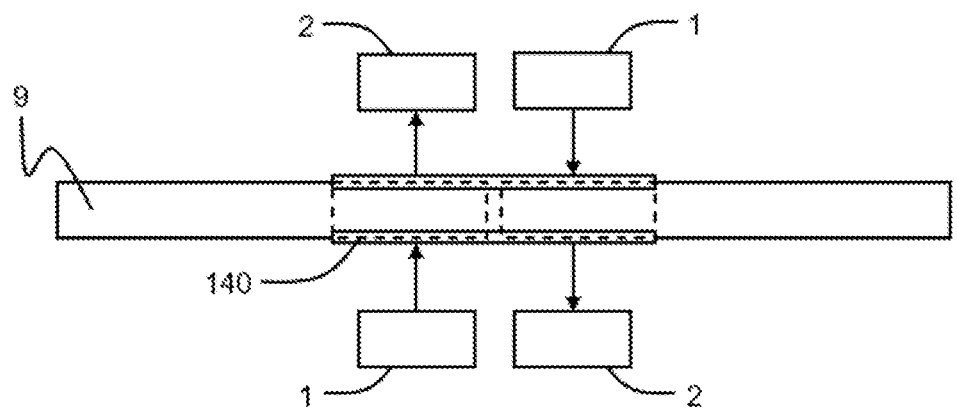
FIG. 4 is a schematic representation of a tint measuring device according to a fourth embodiment of the invention.

The present invention may be further used for making combinations of the first and second embodiments of the invention, as described above. As an example, FIGS. 3 and 4 show schematically a third and a fourth embodiment, respectively, of the invention wherein emission of light by the at least one light source 1 and reception of the reflected or the transmitted light signal each take place on both sides of fluid flow stream 9. According to the third embodiment of the invention, the light signal reflected from the surface of the fluid is measured on both sides of fluid flow stream 9. According to the fourth embodiment of the invention, the light signal transmitted through the fluid is also measured on both sides of fluid flow stream 9. In the two cases, it may be advantageous to emit pulsed, synchronized light so as to prevent the reflected or transmitted light signals from intersecting.

The embodiments using transmission of the light signal through the fluid make it possible in particular to limit impact of the tint gradients in the thickness of fluid flow stream 9 on the tint measurements, especially when the thickness of the fluid flow path or the viscosity of the fluid are high.

The invention will now be described in detail in the context of the non-limiting configuration of the first embodiment of the invention; namely, emission of light by the at least one light source 1 and reception of the light signal reflected from the fluid take place on the same side of fluid flow stream 9. It should be noted that the elements described below may be transposed to the context of a configuration using the measurement of tint by optical transmission of the light signal through the fluid.

As shown in FIG. 5A, tint measuring device 10 preferably includes an end body 7 encapsulating the ends of at least one lighting optical fiber 5 and at least one acquisition optical fiber 4.

Alternatively, end body 7 may only encapsulate the end or the ends of the at least one acquisition optical fiber 4. However, the configuration of end body 7 encapsulating, in the same body, the at least one optical lighting fiber 5 and acquisition fiber 4, facilitates design and use of tint measuring device 10 according to the invention.

The end or the ends are encapsulated in end body 7 so that they open on a face 73 of end body 7 configured for facing measurement zone 140.

Tint measuring device 10 further includes an observation window 8 arranged tangentially to fluid flow stream 9. Observation window 8 includes, for example, a lens.

Observation window 8 is able to withstand a security pressure greater or equal to 1000 bar.

Tint measuring device 10 further includes a holding element 81 mounted in chamber 6, for example opaque, so as to hold observation window 8 in position and to provide leak-tightness to fluid flow stream 9.

Observation window 8 may be, in particular, a porthole, as may be seen in FIG. 5A, which shows an example of an embodiment of tint measuring device 10 according to the invention.

Holding element 81 may, as an example, include a seal encircling observation window 8.

End body 7 is configured for being inserted, at least partially, in particular in a removable manner, for example into chamber 6, for example opaque, so as to position end body 7 facing observation window 8. End body 7 advantageously has the shape of a pencil, in other words a substantially tubular shape so as to simplify the operations of assembling or disassembling end body 7, e.g. for maintenance of tint measuring device 10. Thus, end body 7 advantageously makes it possible to carry out maintenance of tint measuring device 10 as a background task during spraying of the fluid, in other words without disturbing flow of the fluid through stream 9.

With reference to FIG. 5A, end body 7 may advantageously be attached to chamber 6, for example opaque, inter alia by screwing onto a bolt 63. Preferentially, end body 7 is configured for being screwed only over a quarter of a turn, in order to avoid entangling the optical fibers and to facilitate mounting of tint measuring device 10 according to the invention. In order to improve holding of end body 7, chamber 6, for example opaque, may include a mechanical locking element 61, e.g. a pin, preventing rotation of end body 7.

Moreover, with reference to FIG. 5A, chamber 6, for example opaque, includes in particular, a pressing box 62 so as to provide holding of the optical fibers.

Alternatively to bolt 63, end body 7 is provided with a loose or rotating nut, more specifically on a distal portion of end body 7, the distal portion being arranged opposite the ends of the fibers or opposite face 73.

The loose or rotating nut is secured to end body 7, but does not transmit to end body 7 any movement of rotation of screwing or tightening applied to the nut in a normal operation of the loose or rotating nut.

The loose or rotating nut is intended to be screwed on chamber 6.

Such a loose or rotating nut allows avoiding any twisting of the fibers, insofar as the movement for screwing the loose or rotating nut to chamber 6 is not transmitted to the fibers.

Moreover, end body 7 preferably includes an anti-reflection element arranged to optically isolate the at least one lighting optical fiber 5 and the at least one acquisition optical fiber 4 from each other, so as to limit the direct transmission of light from the at least one lighting optical fiber 5 to the at least one acquisition optical fiber 4.

The anti-reflection element advantageously makes it possible to limit the light pollution of acquisition optical fibers 4 by lighting optical fibers 5. More specifically, such an anti-reflection element limits light pollution of the measurement made from the at least one acquisition optical fiber 4 by light that would be directly reflected from the at least one lighting optical fiber 5 toward the at least one acquisition optical fiber 4, without being reflected from the fluid.

The anti-reflection element is, for example, an O-ring, more particularly made of rubber or elastomer.

Preferentially, with reference to FIGS. 5A and 6, end body 7 has a central axis 71. The ends of the at least one lighting optical fiber 5 and the at least one acquisition optical fiber 4, are then distributed circularly around central axis 71 of end body 7, at two different radial distances from central axis 71, respectively, of end body 7.

The at least one acquisition optical fiber 4 is, for example, a single acquisition fiber whose end is arranged on central axis 71. The at least one lighting optical fiber 5 includes a plurality of lighting fibers distributed around central axis 71 and arranged on a circle centered on central axis 71.

The antireflection element is arranged between the ends of the at least one lighting optical fiber 5 on the one hand, and the ends of the at least one acquisition fiber 4 on the other hand. More particularly, the antireflection element is arranged around central axis 71 between the two radial distances.

In an embodiment illustrated in FIG. 6, end body 7 includes an annular recess 72 on face 73 configured for facing measurement zone 140, annular recess 72 being arranged in a portion about central axis 71 and having a radius lying between the two radial distances. End body 7 then includes the anti-reflection element, e.g. a seal, housed in annular recess 72 so as to optically isolate the at least one lighting optical fiber 5 and the at least one acquisition optical fiber 4 from one another.

Alternatively, end body 7 includes a recess in the shape of a disc on face 73 configured for facing measurement zone 140. The recess thus extends recessed from the rest of face 73.

The recess is centered on central axis 71 and has a radius included between the two radial distances.

The end or ends of the at least one acquisition 4 or lighting 5 optical fiber arranged at the smallest radial distance is or are recessed with respect to the end or ends of the other of the at least one acquisition optical fiber 4 or lighting fiber 5. In the example described above, the end of the acquisition optical fiber 4 along the central axis 71 opens near the recess and is set back from the ends of lighting optical fibers 5.

The anti-reflective element, here an O-ring, is housed in recess 72. More particularly, recess 72 has a radius substantially equal to the outer radius of the O-ring. The O-ring is inserted into recess 72 and is held in the recess by contact with the edges of the recess.

Further, the antireflection element has a height, measured along the direction of central axis 71 when the antireflection element is inserted into recess 72, annular or in the form of a disc, so that the antireflection element protrudes from face 73 in the absence of any additional constraints. More particularly, the antireflection element has a height strictly greater than the height of recess 72.

When end body 7 is fixed to chamber 6, face 73 extends facing observation window 8, more particularly the lens of observation window 8.

More particularly, when fixing end body 7 to chamber 6, in particular by bolt 63 or by the loose or rotating nut, a force is applied to end body 7 towards observation window 8. Thus, when the fixing is tightened, in particular by tightening bolt 63 or the loose or rotating nut, the O-ring presses between recess 72 and face 73. Thus, no light pollution is likely to pass at this level. Face 73 comes, for example, in contact with observation window 8 after tightening.

Figure 5B:
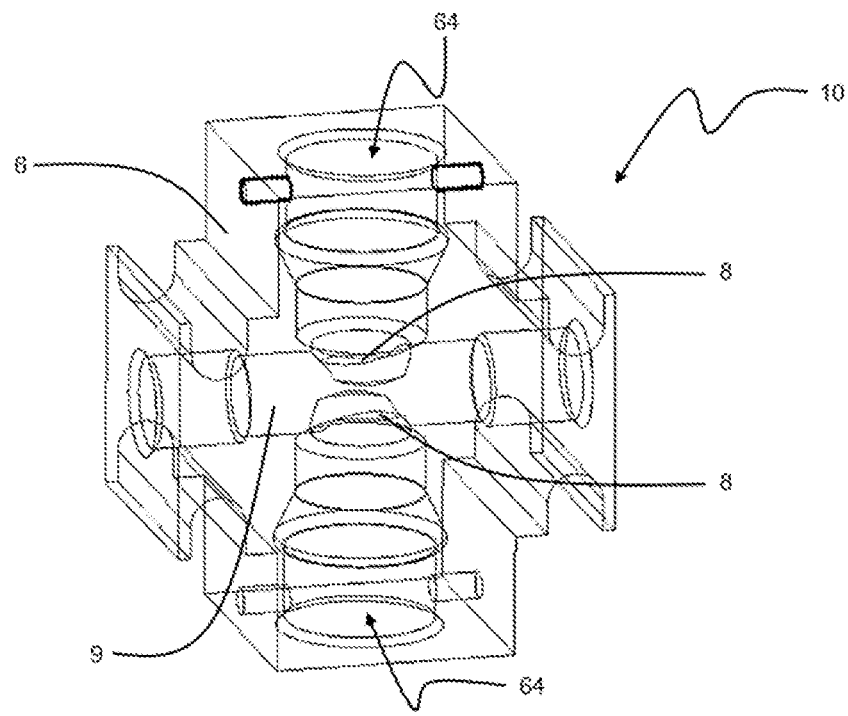
FIG. 5B is a schematic representation of a partial view of another example of a tint measuring device according to another embodiment of the invention.

As expressed above, tint measuring device 10 according to embodiments of the invention may also be configured for performing a tint measurement by transmission of the light signal through the fluid. Where appropriate, as shown in FIG. 5B, tint measuring device 10 advantageously includes two end bodies 7 encapsulating each of the ends of the lighting 5 and/or acquisition optical fibers 4.

Tint measuring device 10 further includes two observation windows 8 arranged tangentially to fluid flow stream 9 and facing each other.

The two end bodies 7 are arranged facing each other, here along the central axis of each end body 7, which are coincident here, each end body 7 extending facing a respective observation window 8.

Tint measuring device 10 includes, for example, two end bodies 7 as described above. In an alternative embodiment, end body 7 is, in this configuration, devoid of antireflection element.

During the measurement, the at least one lighting optical fiber 5 of a first of end bodies 7 is activated and the measurement is performed on the at least one acquisition fiber 4 of the second of end bodies 7. The at least one lighting optical fiber 5 of the second of end bodies 7 is, for example, deactivated, that is, the corresponding light source is turned off.

End bodies 7 are configured for being inserted, at least partially, in particular in a removable manner, into chamber 6, for example opaque, so as to make possible the positioning of each of the two end bodies 7 facing the corresponding observation window 8. The two end bodies 7 are in particular configured for being inserted into two corresponding recesses 64 of chamber 6, here opaque.

In one embodiment, opacity of chamber 6 notably prevents pollution of the measurement by light coming from the environment outside the device.

Moreover, in such a tint measuring device 10 configured for performing tint measurement by transmission of the light signal through the fluid, end bodies 7 may advantageously have features similar to the features described above in the context of the first embodiment of the invention. In the same way, tint measuring device 10 may include two holding elements mounted in chamber 6 so as to hold each of the two observation windows 8 in position, respectively, and to provide leak-tightness of fluid flow stream 9. The two end bodies 7 may also be attached to chamber 6 as described above, in particular with a bolt or a loose nut, a mechanical locking element, and a stuffing box.

Furthermore, with reference to FIG. 1, tint measuring device 10 may be configured for transmitting results of the analysis of the fluid to a control unit 130 configured for controlling a valve or a set of valves 150 of the paint dispensing system, depending on the results of the spectral analysis. Thus, it is possible, e.g., to optimize the operations of changing the tint, or to adjust composition of the paint.

According to another aspect of the invention, with reference to FIG. 1, embodiments of the invention relate to a fluid dispensing system 100 including a fluid flow circuit 120 and a tint measuring device 10 connected in series with fluid flow circuit 120. E.g., as described above, fluid dispensing system 100 may consist of a paint dispensing system.

Figure 7:
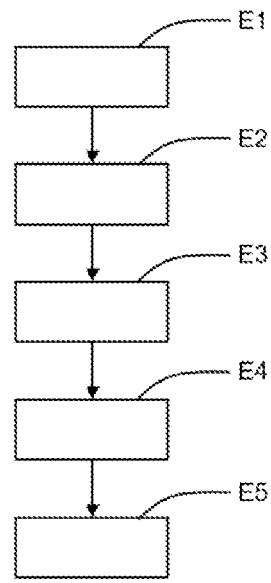
FIG. 7 is a schematic representation of a tint measuring method according to one aspect of the invention.

According to another aspect of the invention, as shown in FIG. 7, the invention relates to a method of measuring the tint of a fluid flowing in a fluid flow circuit using tint measuring device 10 as described above.

The tint measurement method according to such other aspect of the invention includes the following operations:
  emitting E1 polychromatic light toward the fluid by the at least one light source;
  receiving E2, by the light sensor, the light signal either reflected from or transmitted through the fluid;
  performing a spectral analysis E3, by the computing unit, of the light signal received by the light sensor so as to determine a chromatic signature of the fluid; and
  comparing E4 of the chromatic signature of the fluid with a chart of target chromatic signatures, by computing unit 3, so as to determine the tint of the fluid.

In one embodiment, analysis of the fluid further includes determining a brightness level of the light signal received by the light sensor, here by computing unit 3.

The preceding operations may advantageously be repeated regularly at a predetermined frequency, so as to obtain a time evolution of the chromatic signature of the fluid, and possibly of the brightness level.

Advantageously, spectral analysis E3 of the light signal includes decomposing the light signal in the RGB color system, the chromatic signature of the fluid including an RGB color code, corresponding to a given moment. Thus, it is possible to obtain a time evolution of the RGB color code of the fluid.

In the context of using the RGB color system, the set of target chromatic signatures includes the RGB color code table.

Moreover, it is advantageous to use the tint measurement method during an operation of change of tint of the fluid in fluid flow circuit 120. Then, with reference to FIG. 7, the tint measurement method may include determining E5 that the operation of change of tint is completed when the chromatic signature of the fluid reaches a target chromatic signature for a predefined period of time, the target chromatic signature consisting of a subset of the target chromatic signature chart.

In one embodiment, the tint measurement method, carried out during operation of rinsing and/or of tint intensification in fluid flow circuit 120, includes determining that the operation is completed when the fluid chromatic signature reaches a target chromatic signature for a predefined time, as previously disclosed, and/or when the brightness level reaches a user-predefined desired value (threshold).

According to another embodiment of the invention, the invention relates to a method of dispensing paint including the tint measuring method as described above.

As described above, the operations of change of tint of the fluid in fluid flow circuit 120 include inter alia the operations of tint intensification, of change of color, or of rinsing.

Detection by transmission is, for example, implemented for a fluid that is a little opaque, in particular during rinsing.

Detection by reflection is, for example, implemented for an opaque fluid, for example during tint intensification or a mixture of products.

Figure 8:
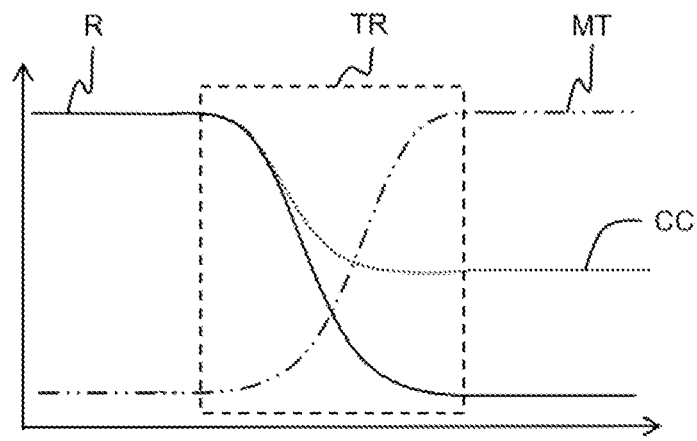
FIG. 8 is a schematic representation of the time evolution of chromatic signatures during tint change operations.

FIG. 8 shows a schematic illustration of time evolutions in the chromatic signature of the fluid for different operations of change of tint carried out in the transition zone TR. Tint intensification MT, e.g., corresponds to flow of a first color instead of an initial solvent through fluid flow circuit 120. In a second example, change of color CC corresponds to a transition from a first color to a second color. In a third example, rinsing R corresponds to circulation of a solvent for cleaning fluid flow circuit 120 of the paint. The present invention has the substantial advantage of optimizing rinsing, which is a critical operation, since poor rinsing may damage the paint dispensing system, and can last for a long time. Moreover, with regard to rinsing, the tint measurement method advantageously makes it possible to monitor the color of the solvent and to estimate whether a part of the solvent may be reused, if appropriate, in order to save material.

Moreover, the tint measurement method may further identify the presence of air bubbles in the fluid, e.g. for monitoring the starting and stopping of the pump configured for providing the fluid of flow. The presence of air bubbles in the fluid show as instabilities in the raw data of the time evolution of the RGB color code of the fluid and of the brightness.

In summary, the present invention has the considerable advantage of making it possible to automatically optimize operations of change of tint. As a result, duration of operations of change of tint is reduced and waste of the fluid components is limited.

Moreover, the invention may further be used for verifying the composition of the mixture of the fluid, for mixtures having a limited number of components, such as for paint, e.g. a mixture of two or three components. In the context of a painting operation, the invention may be used for monitoring the mixture of color and catalyst.

Moreover, tint measuring device 10 according to the invention has an improved autonomy. It is known, e.g., how to produce a conventional paint dispensing system wherein the operations of change of tint are carried out over a predetermined period of time. Determination of such duration is complex, as same depends on several parameters, including the fluids involved, or the volume of the ducts of the fluid flow circuit. Thus, in comparison with such a conventional paint dispensing system, the user no longer has to reprogram operations of change of tint according to the specificities of the fluids involved.

The invention may be further used for performing automatic sorting according to the tint of fluids, inter alia to perform intelligent waste sorting.

The invention claimed is:

1. A tint measuring device configured for being connected in series in a fluid flow path, the tint measuring device comprising:
    at least one light source configured for emitting polychromatic light towards the fluid in a measurement zone;
    a light sensor configured for receiving a light signal either reflected from or transmitted through the fluid, the reflected or the transmitted light signal corresponding to the optical reflection or the optical transmission, respectively, by the fluid, of the polychromatic light emitted in the direction of the fluid by said at least one light source;
    a computing unit configured for performing spectral analysis of the light signal received by said light sensor and for determining a chromatic signature of the fluid;
    at least one acquisition optical fiber configured for routing the light signal either reflected from or transmitted through the fluid to the light sensor, the light sensor being remote from the measurement zone; and
    an opaque chamber through which a fluid flow stream is formed, configured for being connected on both sides to the fluid flow circuit, the opaque chamber housing one end of each of said at least one acquisition optical fiber.

2. The tint measuring device according to claim 1, further comprising:
    an end body encapsulating the end or ends of said at least one acquisition optical fiber;
    an observation window arranged tangentially to the fluid flow stream; and
    a holding member mounted in an opaque chamber for holding said observation window in position and for proving leak-tightness to the fluid flow stream, said end body being configured for being inserted in a removable manner into the opaque chamber, or into a pressing box of the opaque chamber, so as to position said end body facing said observation window.

3. The tint measuring device according to claim 1, wherein the tint measuring device comprises an end body encapsulating the end or ends of said at least one acquisition optical fiber.

4. The tint measuring device according to claim 1, wherein said computing unit is further configured for determining a brightness level of the light signal received by said light sensor.

5. A fluid dispensing system comprising:
    a fluid flow circuit; and
    the tint measuring device according to claim 1, connected in series in said fluid flow circuit.

6. The fluid dispensing system according to claim 5, consisting of a paint dispensing system.

7. A method of measuring tint of a fluid flowing through a fluid flow stream using a tint measuring device according to claim 1, the method comprising:
    emitting polychromatic light towards the fluid by the at least one light source of the tint measuring device;

receiving, by the light sensor of the tint measuring device, a light signal either reflected from the fluid or transmitted through the fluid;

performing a spectral analysis, by the computing unit of the tint measuring device, of the light signal received by the light sensor so as to determine a chromatic signature of the fluid; and comparing the chromatic signature of the fluid with a chart of target chromatic signatures, by the computing unit of the tint measuring device, so as to determine a tint of the fluid.

8. The tint measuring method according to claim 7, further comprising determining a brightness level of the light signal received by the light sensor of the tint measuring device.

9. The tint measuring method according to claim 7, carried out during a change of tint of the fluid in the fluid flow circuit, wherein the method further comprises determining that the change of tint is completed when the chromatic signature of the fluid reaches a target chromatic signature for a predefined time, the target chromatic signature comprising a subset of the chart of target chromatic signatures.

10. A paint dispensing method comprising the tint measuring method according to claim 9, wherein the change of tint of the fluid in the fluid flow circuit comprises tint intensification, change of color, or rinsing.

11. A tint measuring device configured for being connected in series in a fluid flow path, the tint measuring device comprising:
at least one light source emitting polychromatic light towards the fluid in a measurement zone;
a light sensor receiving a light signal either reflected from or transmitted through the fluid, the reflected or the transmitted light signal corresponding to the optical reflection or to the optical transmission, respectively, by the fluid, of the polychromatic light emitted in the direction of the fluid by said at least one light source;
a computing unit configured for performing spectral analysis of the light signal received by said light sensor and for determining a chromatic signature of the fluid;
at least one acquisition optical fiber configured for routing the light signal either reflected from or transmitted through the fluid to said light sensor, said light sensor being remote from the measurement zone;
at least one lighting optical fiber connected at one end to said at least one light source and configured for routing the polychromatic light from said at least one light source toward the fluid;
an end body encapsulating the end or ends of said at least one acquisition optical fiber and the end or ends of said at least one lighting optical fiber; and
an anti-reflection element arranged so as to optically isolate said at least one lighting optical fiber and said at least one acquisition optical fiber from each other, so as to limit the direct transmission of light from said at least one lighting optical fiber to said at least one acquisition optical fiber.

12. The tint measuring device according to claim 11, wherein said end body has a central axis, wherein the ends of said at least one lighting optical fiber and said at least one acquisition optical fiber are distributed circularly around the central axis of said end body at two different radial distances from the central axis, respectively, of said end body.

13. The tint measuring device according to claim 12, wherein said end body comprises a recess, annular or in the form of a disc, on a face configured for facing the measurement zone, the recess being arranged in a portion around the central axis and having a radius comprised between the two different radial distances, said end body comprising said anti-reflection element housed in the recess so as to optically isolate said at least one lighting optical fiber and said at least one acquisition optical fiber from each other.

\* \* \* \* \*